United States Patent
Hao et al.

(10) Patent No.: US 10,835,548 B2
(45) Date of Patent: Nov. 17, 2020

(54) METRONOMIC ORAL GEMCITABINE FOR CANCER THERAPY

(71) Applicant: InnoPharmax, Inc., Taipei (TW)

(72) Inventors: Wei-Hua Hao, Taipei (TW); Shu-Ping Hsueh, Taipei (TW); Chang-Shan Hsu, Taipei (TW)

(73) Assignee: INNOPHARMAX, INC., Taipei (TW)

( * ) Notice: Subject to any disclaimer, the term of this patent is extended or adjusted under 35 U.S.C. 154(b) by 0 days.

(21) Appl. No.: 15/612,116

(22) Filed: Jun. 2, 2017

(65) Prior Publication Data

US 2017/0348341 A1 Dec. 7, 2017

Related U.S. Application Data

(60) Provisional application No. 62/344,660, filed on Jun. 2, 2016.

(51) Int. Cl.
| | |
|---|---|
| *A61K 31/7068* | (2006.01) |
| *A61K 9/00* | (2006.01) |
| *A61K 9/107* | (2006.01) |
| *A61K 47/26* | (2006.01) |
| *A61K 9/48* | (2006.01) |
| *A61K 47/10* | (2017.01) |

(52) U.S. Cl.
CPC ........ *A61K 31/7068* (2013.01); *A61K 9/0053* (2013.01); *A61K 9/107* (2013.01); *A61K 9/48* (2013.01); *A61K 47/10* (2013.01); *A61K 47/26* (2013.01)

(58) Field of Classification Search
CPC ... A61K 31/7068; A61K 9/0053; A61K 9/107
USPC ........................................................ 514/49
See application file for complete search history.

(56) References Cited

U.S. PATENT DOCUMENTS

| | | | |
|---|---|---|---|
| 8,735,394 B2 | 5/2014 | Desai et al. | |
| 8,906,353 B2 | 12/2014 | Eldon et al. | |
| 9,101,543 B2 | 8/2015 | Desai et al. | |
| 2010/0273730 A1 | 10/2010 | Hsu et al. | |
| 2015/0283237 A1 | 10/2015 | Felder et al. | |

FOREIGN PATENT DOCUMENTS

WO   WO 2010039039 A1 *   4/2010

OTHER PUBLICATIONS

Veltkamp et al. (Clip Cancer Res 2008;14(11) Jun. 1, 2008, 3477-3486).*
Cao et al., 2010, Mol. Cancer Ther. 9(7):2068-2078.
Cham et al., 2010, Br. J. Cancer 103:52-60.
Fossella et al., 1997, J. Clin. Oncol. 15:310-316.
Francia et al., 2012, Mol. Cancer Ther. 11:680-689.
Hasnis et al., 2014, Neoplasia 16:501-510.
Khan et al., 2014, Adv. Exp. Med. Biol. 812:105-111.
Laquente, 2008, Mol. Cancer Ther. 7(3):638-647.
Malik et al., 2014, Frontiers Oncol. 4:Art. 76: 1-7.
Pietras et al., 2005, J. Clin. Oncol. 23:939-952.
Pratt et al., 2013, Mol. Cancer Ther. 12(4):481-490.
Shevchenko et al., 2013, Int. J. Cancer 133:98-107.
Tongu et al., 2013, Cancer Immunol. Immunother. 62:383-391.
Vives et al., 2013, Int. J. Cancer 133:2464-2472.
Yapp et al., 2016, 19:229-244.
Yi et al., 2014, Cancer Biomark. 14:427-433 (Abstract Only).
Faivre et al., 2012, J. Clin. Oncol. 30(15):Suppl. p. 2554 (Abstract Only).

* cited by examiner

*Primary Examiner* — Shaojia A Jiang
*Assistant Examiner* — Michael C Henry
(74) *Attorney, Agent, or Firm* — Birch, Stewart, Kolasch & Birch, LLP

(57) ABSTRACT

The disclosure relates to compositions and methods for treatment, such as inducing regression or inhibiting growth, of tumors in a patient such as a human. Use of gemcitabine, including in self-emulsifying orally administered dosage forms for these purposes is described. Gemcitabine is orally administered in a metronomic manner, which involves repeatedly administering a therapeutic amount of gemcitabine, being a fraction of the maximum tolerated dose, over an extended period of time, preferably on a non-interrupted schedule of weeks, months, or indefinitely.

25 Claims, 8 Drawing Sheets

METRONOMIC ORAL GEMCITABINE FOR CANCER THERAPY

CROSS-REFERENCES TO RELATED APPLICATIONS

This application is entitled to priority to U.S. provisional patent application No. 62/344,660 filed 2 Jun. 2016, that application being incorporated herein by reference.

BACKGROUND OF THE DISCLOSURE

The invention relates generally to the field of use of oral therapeutic agents, including gemcitabine, for treatment of certain tumors.

Oral administration is a convenient and user-friendly mode of drug administration, either in the form of a solid or a liquid suspension, which continues to dominate the area of drug delivery technologies. Even though many types of drugs could be administered orally with acceptable efficacy, there remains a problem for some classes of drugs, especially those which are known to have good solubility, but are extensively metabolized in the liver, easily pumped out by the intestinal epithelium (poor permeability) or irritative to the gastric mucosa, such as Class III drugs of Biopharmaceutics Classification System (BCS) provided by the U.S. Food and Drug Administration. For these drugs, of which the therapeutic agent gemcitabine (GEM) is one, injection administration become the major option to achieve acceptable drug absorption and bioavailability which however leads to increased risk and expenses and further is painful for patients.

Pharmaceutical compositions for oral administration of relatively hydrophilic drugs such as GEM have been described. For example, U.S. patent application publication number 2010/0273730 of Innopharmax, Inc. describes self-emulsifying preparations of such drugs which exhibit good bioavailability (i.e., comparable to that attained through intravenous injection) and storage stability of the drug.

GEM has been described for use to treat a variety of carcinomas. In order to achieve maximal anti-tumor effect, GEM is often administered intravenously at the maximum dose that is, or is likely to be, tolerated by the patient (the "MTD"). A shortcoming of existing GEM therapies is that the drug can suppress production of blood cells in patients, especially when used at MTD.

"Metronomic" chemotherapy has been described by others (e.g., Sharovsky et al., 2009, Curr. Oncol. 16(2):7-15). This name makes reference to chronic, approximately equally spaced administration of (generally) low doses of chemotherapeutic drugs without extended rest periods. Metronomic therapy involves administration of drugs well below their MTD. Metronomic dosing of GEM has been described by others, but only in the contexts of either injecting GEM or orally administering a prodrug (designated LY2334737) intended to be metabolized to form GEM following ingestion. See e.g., Yapp et al., 2016, Angiogenesis 19:229-244; Hasnis et al., 2014, Neoplasia 16:501-510; Vives et al., 2013, Int. J. Cancer 133:2464-2472; Pratt et al., 2013, Mol. Cancer Ther. 12:481-490; Francia et al., 2012, Mol. Cancer Ther. 11:680-689; Cham et al., 2010, Br. J. Cancer 103:52-60; Laquente et al., 2008, Mol. Cancer Ther. 7:638-647. Oral metronomic dosing of GEM itself has not been shown effective, presumably on account of low bioavailability attributable to extensive first-pass metabolism. Veltkamp et al. 2008, Clin. Cancer Res. 14:3477-3486.

It would be advantageous if an effective anti-cancer therapy were developed which avoids both the disadvantages of parenteral administration (e.g., discomfort and need for professional administration) and the vagaries of prodrug administration (e.g., variability of prodrug metabolism among patients) and instead delivers an effective amount of an anti-cancer therapeutic agent in an orally-administered form. The present disclosure describes such therapy.

BRIEF SUMMARY OF THE DISCLOSURE

This disclosure relates to methods of treating GEM-sensitive tumor in subjects of a species. These methods include orally administering to the subject a dosage form that includes a therapeutically-effective amount of GEM in a formulation that, upon oral ingestion, releases in a bioavailable form less than half the maximum tolerated dose (MTD) of GEM for the species. By way of example, the formulation can be one which spontaneously forms an emulsion upon contacting an aqueous medium at 37 degrees Celsius under mild mechanical agitation, (i.e., conditions like those within the gastrointestinal tract of a human subject). The formulation can be administered to the subject multiple times, such as at an interval of two or three days between successive administrations.

In a preferred embodiment, the formulation includes at least three components, namely (a) GEM dissolved in a hydrophilic solvent; (b) a surfactant system that exhibits a hydrophilic-lipophilic balance (HLB) value of from about 8 to about 17 and that includes at least one surfactant; and (c) a hydrophilic carrier that is compatible both with the GEM-solvent solution and with the surfactant system. By way of example, one such formulation described herein ("GEMORAL") is a combination of GEM (or a pharmaceutically acceptable salt of GEM), water, glycerol, PEG, polysorbate, and oleoyl polyoxylglycerides. Formulations as described herein can be administered in the form of capsules, such as soft capsules.

The compositions described herein are useful for treating GEM-sensitive tumors, such as tumors of the breast, bladder, pancreatic, and bile duct, as well as non-small cell lung tumors in humans. To treat such tumors in humans, GEM can be administered in formulations which release not more than, for example, $\frac{1}{3}$, $\frac{1}{4}$, $\frac{1}{5}$, $\frac{1}{6}$, $\frac{1}{7}$, $\frac{1}{10}$, $\frac{1}{12}$, $\frac{1}{15}$, $\frac{1}{20}$, or $\frac{1}{40}$ of the MTD of GEM for humans when administered by the same route.

Another aspect of what is disclosed herein are methods of inducing regression of a GEM-sensitive tumor in a human patient. These methods are performed substantially similarly to those described above, namely by orally administering to the patient a therapeutically-effective amount of GEM in a formulation that, upon oral ingestion, releases in a bioavailable form less than half the MTD of GEM for the patient.

In yet another aspect of what this disclosure teaches are methods of inhibiting growth of a tumor in a human patient. These methods are likewise practiced by orally administering to the patient a therapeutically-effective amount of GEM in a formulation that, upon oral ingestion, releases in a bioavailable form less than half the MTD of GEM for the patient.

The present invention also discloses GEM for use in treating a GEM-sensitive tumor or inducing regression of a GEM-sensitive tumor in a subject of a species, wherein GEM is to be orally administered to the subject in a formulation that upon oral ingestion, releases in a bioavailable form less than the MTD of GEM for the species as described herein. Also provided is use of GEM for the manufacture of a medicament for treating a GEM-sensitive tumor or inducing regression of a GEM-sensitive tumor in a subject of a species wherein GEM is to be orally administered to the subject in a formulation that upon oral ingestion, releases in a bioavailable form less than the MTD of GEM for the species as described herein.

The present invention also discloses GEM for use in inhibiting growth of a tumor in a human patient, wherein GEM is to be orally administered to the subject in a formulation that upon oral ingestion, releases in a bioavailable form less than the MTD of GEM for the patient as described herein. Also provided is use of GEM for the manufacture of a medicament for inhibiting growth of a tumor in a human patient, wherein GEM is to be orally administered to the subject in a formulation that upon oral ingestion, releases in a bioavailable form less than the MTD of GEM for the patient as described herein.

This disclosure also relates to manufacture of medicaments useful for practicing the methods described herein. That is, methods are disclosed for making orally-administrable formulations which include a therapeutically-effective amount of GEM in a formulation that, upon oral ingestion, releases in a bioavailable form less than half the MTD of GEM for the species. Such formulations can be ones which spontaneously form an emulsion upon contacting an aqueous medium at 37 degrees Celsius under mild mechanical agitation, (i.e., conditions like those within the gastrointestinal tract of a human subject). The formulations can be administered to the subject multiple times, such as at an interval of two or three days between successive administrations.

Formulation which can be made as described herein can include at least three components, namely (a) GEM dissolved in a hydrophilic solvent; (b) a surfactant system that exhibits a hydrophilic-lipophilic balance (HLB) value of from about 8 to about 17 and that includes at least one surfactant; and (c) a hydrophilic carrier that is compatible both with the GEM-solvent solution and with the surfactant system. By way of example, one such formulation described herein ("GEMORAL") is a combination of GEM (or a pharmaceutically acceptable salt of GEM), water, glycerol, PEG, polysorbate, and oleoyl polyoxylglycerides. Formulations as described herein can be made in the form of capsules, such as soft capsules.

DETAILED DESCRIPTION

Figure 1:
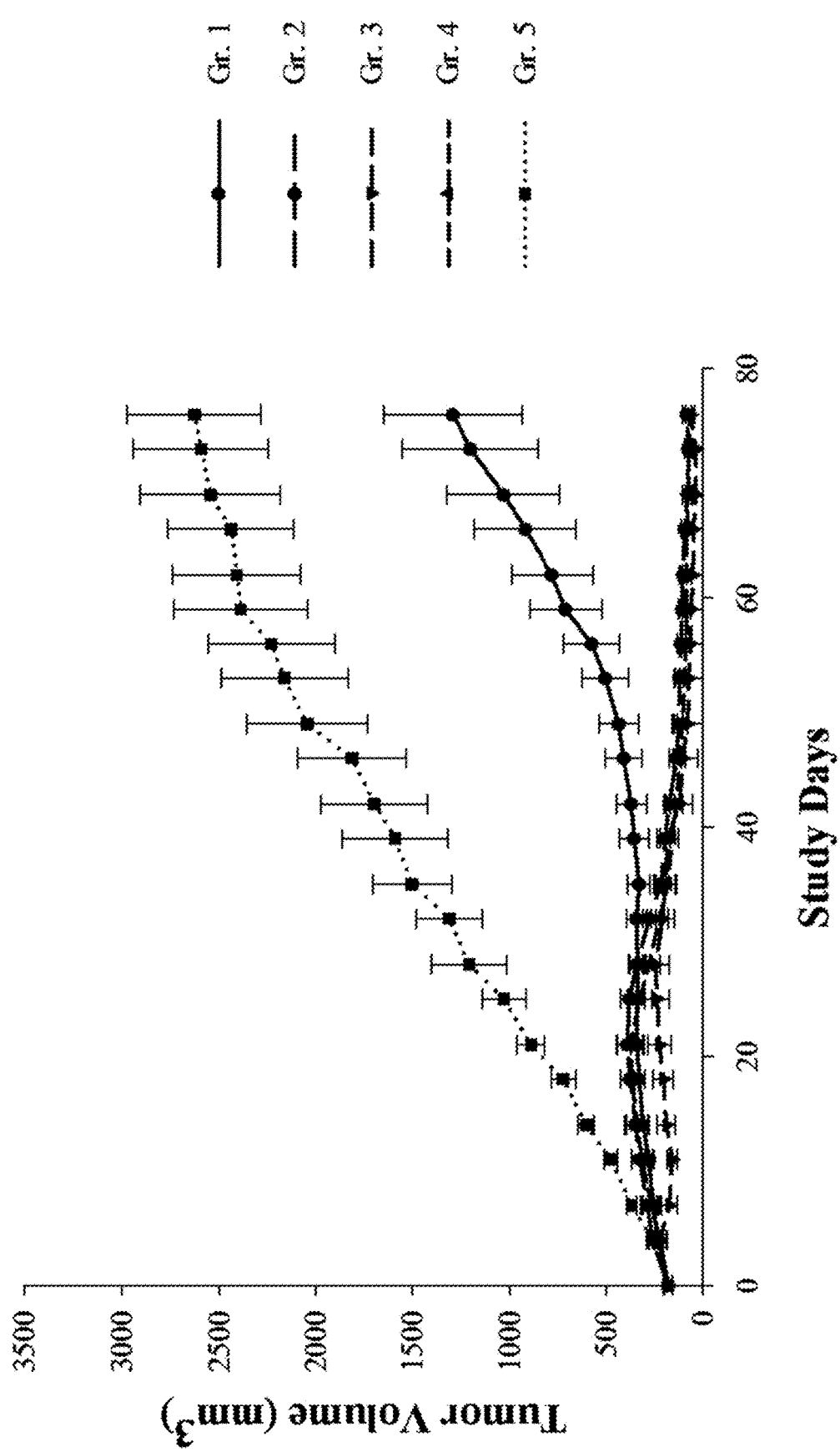
FIG. 1 is a graph of tumor volume over time for animals to which a patient-derived human cholangiocarcinoma had been xenografted. Further details are described in Example 2.

The disclosure relates to compositions and methods for orally administering gemcitabine (GEM) to subjects in order to treat a tumor in the subject. Such treatment can include reducing the volume, weight, or rate of growth of the tumor, for example, and can also include inducing regression of the tumor.

Use of GEM as an anti-cancer agent has long been known. However, use of GEM has long been limited to injection of the drug or oral administration of prodrugs which are hoped/expected to be metabolized within a patient's body to yield GEM.

Described herein are data demonstrating that GEM itself can be orally administered in a metronomic fashion, either as a monotherapy or a supplement to another anti-tumor therapy, and will exert an effective anti-tumor effect. Although the data presented herein were gathered using non-human animal xenograft models of human cholangiocarcinomas and pancreatic cancers, a skilled artisan will appreciate that the data indicate the usefulness of the therapies described herein for treating or alleviating these tumors in human patients. A skilled artisan will furthermore recognize from the information presented herein that oral metronomic administration of GEM can be expected to exert favorable anti-tumor effects against all human tumors known or later discovered to be responsive to GEM therapy (e.g., those responsive to injected GEM, including at least certain breast, bladder, pancreatic, bile duct, and non-small cell lung cancers).

We have discovered that injection of GEM (e.g., intraperitoneally or intravenously) at a higher dose (e.g., a dose at or near the maximum tolerated dose, MTD), followed by metronomic oral administration of a substantially lower dose of GEM can yield greater tumor regression than injection alone. The oral dose can, for example, be a self-emulsifying preparation of GEM, such as is described in U.S. patent application publication number 2010/0273730, and can include a fraction of the MTD, such as ½, ⅓, ¼, ⅕, ⅙, 1/7, 1/10, 1/12, 1/20, or 1/40 the MTD of GEM.

We have also discovered that metronomic oral administration of GEM at a dose substantially lower than the MTD can induce tumor regression, even in the absence of injection of GEM, or following treatment with a different anti-tumor agent, such as 5-fluorouracil (5FU).

Metronomic Oral Administration of GEM

An important aspect of the subject matter described herein is the discovery that GEM exhibits significant anti-tumor effects when administered orally in a bioavailable form, at a dosage substantially lower than the maximum tolerated dose (MTD) of GEM, and especially when administered regularly over an extended period of time (e.g., weeks, months, or years). Such administration is generically referred to as "metronomic" administration and has been considered an effective treatment regimen for some other anti-tumor agents. Prior to the present disclosure, however, it was unknown whether GEM would exhibit significant anti-tumor effects when orally administered as part of a metronomic regimen and how a GEM metronomic regimen works.

GEM has previously been shown to inhibit tumor growth when administered orally at a dose near the MTD. However, following discontinuation of MTD-GEM oral administration, the rate of tumor growth rebounds to a rate approximately equal to the rate of tumor growth in otherwise-similar vehicle-treated (i.e., no GEM administered) animals. Owing to the detrimental effects attributable to MTD-GEM oral administration, such therapy can be provided for only limited periods of time. Oral metronomic GEM therapy permits a longer duration of GEM-mediated inhibition of tumor growth rate. Whether administered as a sole therapy or in conjunction with other anti-tumor therapies, oral metronomic GEM therapy extends the period of anti-tumor efficacy.

It is well known that certain anti-tumor drugs, such as GEM, can be administered by non-oral routes (e.g., parenterally or transepithelially). However, the oral route is one by which a large majority of patients are able to tolerate drug administration over relatively long periods of times (e.g., days, weeks, months, years, or even for a lifetime) and for which compliance with drug administration tends to be high. Furthermore, administration of drugs by the oral route can typically be performed in non-clinical settings (e.g., homes or while traveling), whereas administration by other routes (and/or administration of drugs at or near their MTD) can require a visit to or period of confinement in a clinical institution. Because the therapeutic methods described herein can involve only oral administration of GEM at sub-MTD amounts, subjects undergoing such therapeutic methods can remain non-institutionalized and independent. In these ways too, the methods described herein represent a significant advance over previously known anti-tumor methods The MTD of a drug is commonly considered to be the highest dose of a drug that does not cause an unacceptable side effect attributable to the drug in its recipient. In practice, MTD is usually determined empirically, by administering escalating doses of a drug to individuals who are similar to patients expected to receive the drug clinically and by observing side effects experienced by those individuals following-administration. The MTD can be selected by observing the largest dose which induces an unacceptable side effect in a sufficiently small fraction of individuals to whom it is administered (e.g., fewer than ½, ¼, or 10% of individuals). MTD can vary among species, and among routes of administration; thus it is important that the MTD be determined by the corresponding route for a population of individuals analogous to patients expected to receive the drug clinically by the same route.

By way of example, in order to assess MTD for GEM for the xenografted mice described in Example 2, we orally administered the GEMORAL composition described in Example 1 to groups of 5 BALB/c nude mice (initial age 10 weeks) for 28 days at dose levels of 3 or 5 mg/kg per day, or 10 or 20 mg/kg every other day for the various groups. Survival and body weight loss were followed during the four-week study period. The MTD of GEMORAL for daily and every-other administration day were determined to be 3 mg/kg and 10 mg/kg, respectively. All doses are expressed as milligrams per kilogram of GEM free base equivalent.

For GEM, others have determined MTD values for human cancer patients. For example, Fossella et al. (1997, J. Clin. Oncol. 15:310-316) estimated an MTD of 2,400 mg/m$^2$/week for a GEM intravenous infusion regime regime (2,400 mg/m$^2$ corresponding to 3,893 mg/60 kg for a human patient, equal to 64.988 mg/kg). Labeling for a commercial GEM product, marketed under the brand name GEMZAR (Eli Lilly and Co.) recommends an intravenous dosage of 1,000 or 1,250 mg/m$^2$. In details, GEMZAR dosage administration is conducted at a dose of 1,000 mg/m$^2$, corresponding to 1,622 mg/60 kg for a human patient, equal to 27.03 mg/kg, administered on Days 1 and 8 or Days 1, 8, and 15 of a 21-day cycle, or at a dose of 1,250 mg/m$^2$, corresponding to 2,027 mg/60 kg for a human patient, equal to 33.878 mg/kg, administered on Days 1, 8, and 15 of a 28-day cycle.

By way of example, GEM was administered orally to human cancer patients as described in Example 6 in an attempt to determine MTD. No MTD was determined in those experiments, because no dose-limiting toxicity (DLT) was observed over the GEM dosage range studied (0-80 mg). Methods of determining MTD are well known, and a skilled artisan can readily determine MTD for GEM orally administered in the GEMORAL formulation. The experiments described in Example 6 demonstrate that this MTD is greater than 80 mg in the dosing regimen used, meaning that this value can be used as a (low) estimate of MTD for the purposes described herein. That is, a fraction of this dose can be selected as a metronomic dose.

As used herein, "metronomic" administration of an oral formulation of GEM to a subject refers to repeated administration of an oral GEM formulation to a patient afflicted with a GEM-responsive tumor, each dose of the oral GEM formulation containing only a fraction of the MTD of GEM for such subjects, such as one-half, one-third, one-fourth, one-fifth, one-sixth, one-seventh, one-tenth, one-twelfth, one-fifteenth, one-twentieth, or one-fourtieth of the MTD of GEM. The MTD value used for calculating such doses can be a value reported in the art for analogous subjects, a value empirically determined for analogs of such subjects (e.g., phase I study participants), a value estimated by comparison with values for subjects afflicted with a different GEM-responsive tumor, or a combination of these. By way of example, in studies described herein in mice bearing xenografted human tumor tissue, an oral metronomic dose of 10 mg/kg was administered every other day, representing a dose which is approximately one-sixth to one-twelfth the MTD of GEM orally administered every three days to similar mice.

In another embodiment, the oral dose suitable for metronomic administration according to the invention, i.e., the dose of GEM formulation that, upon oral ingestion, releases in a bioavailable form less than half the MTD of GEM for the species, can be selected by using a fraction (as above) of the highest-known "safe" dose. MTD can thus be estimated by observing the highest dose safely tolerated by one or more subjects under the circumstances, and that highest safely-tolerated-dose can be used as an estimate for MTD for the purposes described herein. By way of example, a dose of GEM of 80 mg, orally administered thrice per week (on days 1, 3, 5, 8, 10, and 12) in the GEMORAL formulation was demonstrated to be safe for human patients afflicted with advanced biliary tract cancer (see Example 6; for an average human body weight of 60 kg, the 80 mg dose is equivalent to 1.33 mg/kg). Thus, for example, a fraction of this known-safe dose can be used for metronomic oral administration in this patient population in place of MTD. A metronomic dose should exhibit at least some therapeutic effect upon the tumor to be treated. Thus, for example, so long as at least some minimal therapeutic effect upon the tumor (e.g., reduction in tumor growth rate or shrinkage of tumor mass or volume) is observable, at least after metronomic dosing is continued for at least one month.

In human patients, such as, in particular, patients afflicted with one or more of breast, bladder, pancreatic, bile duct, and non-small cell lung tumors, suitable oral doses of GEM according to the invention include, for example, a fraction of 80 mg (corresponding to 1.33 mg/kg for an average 60 kg human), such as 40 mg (0.67 mg/kg), 27 mg (0.45 mg/kg), 20 mg (0.33 mg/kg), 16 mg (0.27 mg/kg), 11 mg (0.18 mg/kg), 8 mg (0.13 mg/kg), 6.7 mg (0.11 mg/kg), 5.3 mg (0.088 mg/kg), or 4.0 mg (0.067 mg/kg). It is thus provided GEM, for use in treating a tumor, preferably a GEM sensitive tumor, in a subject, preferably a human patient, wherein GEM is administered orally at a dose unit of no more than 50 mg (0.83 mg/kg), preferably less than 40 mg (0.67 mg/kg), still preferably less than 20 mg (0.33 mg/kg). In a preferred embodiment, GEM may be administered orally at a dose unit of between 4 to 40 mg (0.067 to 0.67 mg/kg). Such oral doses may be administered repeatedly, e.g. every 2 to 4 days. Preferably GEM is formulated in a self-emulsifying composition as described below, preferably (a) the GEM dissolved in a hydrophilic solvent; (b) a surfactant system that exhibits a hydrophilic-lipophilic balance (HLB) value of from about 8 to about 17 and that includes at least one surfactant; and (c) a hydrophilic carrier compatible with the GEM-solvent solution and with the surfactant system. Preferably the composition comprises at least a surfactant and polyethylene glycol (PEG), e.g. as in the composition of Example 1. Preferably the treatment lasts at least two or three weeks, or at least one month, 1 to 6 months, or even years, e.g., 1 to 2 years. In a particular embodiment, the doses are administered in the dosing regimen described in Example 6. Similarly, suitable metronomic oral doses of GEM can be determined for these or other GEM-sensitive tumors by determining MTD (or a DLT-free dose usable as a low estimate for MTD) for a desired dosing regimen (as was done in Example 6 for the dosing regimen outlined there) and selecting a fraction of the MTD (or highest determined DLT-free dose) as the suitable dose for the desired regimen.

Metronomic administration colloquially refers to repeated dose administrations that generally proceed on a regular schedule without significant interruptions or "drug holidays," either indefinitely or over a sustained period of time. As used herein, "metronomic" oral administration of GEM means repeated administrations of a fractional-MTD oral formulation of GEM on a regular, non-interrupted schedule. Such a schedule can include dosing frequencies such as thrice-daily, twice-daily, daily (QD), every-other-day (i.e., Q2D), every-third-day (i.e., Q3D), every-fourth-day (i.e., Q4D), every-fifth-day (i.e., Q5D), weekly, twice-weekly, or thrice-weekly dosing schedules, for example. The dosing schedule can be maintained for as long a period of time or for as great a number of doses as desired and as the subject is able to tolerate. Desirably, such metronomic dosing can exert anti-tumor therapeutic effect (e.g., reduction, cessation, or reversal of tumor growth) over a prolonged period, such as months or years (or indefinitely).

The physical form of the oral GEM formulation administered metronomically, as described herein, is not critical. Substantially any oral dosage form that will deliver GEM in a bioavailable form to the gastrointestinal tract of the subject in the amounts and on the schedules described herein can be employed, such as any of the dosage forms described in US published patent application 2010/0273730. Preferably, the oral GEM formulation is administered in the form of a capsule containing the material described in US published patent application 2010/0273730. As an example, such a material might have the composition described in the table of Example 1.

Metronomic administration of an oral formulation of GEM to a subject can, for example, be achieved by administering a single capsule or soft capsule containing the entire dose, by administering multiple capsules or soft capsules each containing a portion of the entire dose, by administering a tablet, or by administering a liquid emulsion to the subject.

Metronomic oral administration of GEM can be used as a monotherapy to treat (e.g., inhibit growth of, decrease size of, or eliminate) a tumor. Metronomic oral administration of GEM can also be performed as an adjunctive treatment before, after, or overlapping with another anti-tumor treatment using GEM or another anti-tumor agent. By way of example, a subject can be treated with a near-MTD (e.g., >1/2 MTD) quantity of GEM or another anti-tumor agent and, following the cessation such treatment, metronomic oral administration of GEM can be performed as described herein. Alternatively, metronomic oral administration of GEM can be begun at the same time as a near-MTD treatment and endure beyond cessation of thereof. As yet another alternative, metronomic oral administration of GEM can be performed and another anti-tumor treatment can be performed during only a part of the period during which metronomic oral administration of GEM occurs. When metronomic oral administration of GEM is performed as an adjunctive treatment, the other treatment can be one which involves oral administration of GEM or another anti-tumor agent, one which involves non-oral (e.g., intravenous or intra-tumor injection) of GEM or another anti-tumor agent, or a non-drug treatment (e.g., tumor resection surgery).

Self-Emulsifying Oral Pharmaceutical Compositions

The subject matter described herein includes a self-emulsifying pharmaceutical (SEP) composition of GEM for oral administration. In addition to GEM, the SEP composition includes one or more solvents for dissolving GEM to form a GEM-solvent solution. The SEP composition also includes a surfactant system. The surfactant system is one or more surfactants which exhibit a hydrophilic-lipophilic balance (HLB) value ranging from about 8 to about 17. In the SEP composition, the GEM-solvent solution and the surfactant system are combined with one or more hydrophilic carriers which are compatible with both the GEM-solvent solution and the surfactant system. When orally administered in the oral SEP composition excellent bioavailability of GEM is observed. Surprisingly, doses of GEM which are thus orally administered can provide the beneficial tumor therapeutic responses described herein. Oral SEP compositions of GEM also exhibits good storage stability.

Accordingly, in one aspect, the present invention provides an oral self-emulsifying pharmaceutical composition for administration to humans, comprising:

(a) a therapeutically effective amount of a GEM or a pharmaceutically acceptable salt of GEM, the amount being a fraction (i.e., less than half) of the MTD for GEM when orally administered to humans in an identical (or substantially similar) SEP composition;

(b) one or more solvents capable of dissolving the drug or salt to form a GEM-solvent solution;

(c) a surfactant system comprising one or more surfactants, the surfactant system exhibiting an HLB value from about 8 to about 17; and (d) one or more hydrophilic carriers which are compatible with the GEM-solvent solution and the surfactant system.

The term "self-emulsifying" is used herein in the same sense as in U.S. patent application publication number 2010/0273730. That is, the term is used to describe a formulation which produces a fine oil-water emulsion when the formulation contacts an aqueous medium (such as when it is combined with water at 37 degrees Celsius and 1 atmosphere pressure with water under mild mechanical agitation, such as gentle stirring or swirling). Preferably, the SEP composition forms an emulsion with a mean particle size of less than 800 nm (more preferably less than 400 nm, 200 nm, or 100 nm, for example, about 10 nm) when it contacts such an aqueous medium.

As used herein, the term "therapeutically effective amount" means a dose of GEM that is effective in exerting a therapeutic effect, particularly a dose of the drug which, after absorption into the body through the walls of gastrointestinal (GI) tract, exerts a detectable therapeutic antitumor effect on a GEM-sensitive tumor of the subject to which the composition is administered. Ordinarily skilled artisans understand that the amounts of GEM included in the composition vary with the particular situation, including but not limited to, the species, size, age and condition of the subject, for example.

As used herein, the term "pharmaceutically acceptable salt" includes, but is not limited to, acid addition salts that substantially retain the biological effectiveness and properties of GEM. Such acid addition salts may be formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, trifluoroacetic acid and the like.

In SEP compositions, one or more solvents are used to dissolve GEM or a GEM salt to form a GEM-solvent solution. Preferably, each of the solvents can dissolve about 1 part (by weight) of GEM or salt in less than 100 parts (or 30, 10, or 1 part) of the solvent. Examples of suitable solvents include water, ethanol, polyethylene glycol (PEG), isopropanol (IPA), 1,2-propanediol (propylene glycol), glycerol, acetic acid, and combinations of these. By way of example, the solvent(s) can be present in an amount ranging from about 2.5% to about 60% (w/w) based on the weight of the SEP composition.

The surfactant system of the SEP composition includes one or more surfactants and exhibits a HLB value ranging from about 8 to about 17. HLB value is known in the art for ranking surfactants according to the balance between the hydrophilic and lipophilic portions of the surfactant agent; the higher the HLB value, the more hydrophilic the surfactant agent; and the lower the HLB value, the less hydrophilic the surfactant agent. A single surfactant having a HLB value ranging from about 8 to about 17 may be used in SEP compositions. Alternatively, a combination of a high HLB surfactant and a low HLB surfactant may be used. The precise choice(s) and identity(ies) of surfactant(s) is not critical so long as the surfactant or combination of surfactants exhibits an HLB value ranging from about 8 to about 17. Suitable surfactants include cationic, anionic, and non-ionic surfactants. Examples of suitable surfactants include polysorbate, poloxamers, oleoyl polyoxylglycerides (such as those sold under trade name LABRAFIL™ M1944CS), linoleoyl polyoxylglycerides (such as LABRAFIL™ M2125CS), caprylocaproyl polyoxylglycerides (such as Labrasol), polyoxyethylene castor oil derivatives (such as PEG 40 hydrogenated castor oil, those sold under trade name CREMOPHOR™ EL or CREMOPHOR™ RH), polyoxyethylene alkyl ethers (such as those sold under trade name BRU™), sorbitan fatty acid esters (such as those sold under trade name SPANS™), glyceryl monooleate (such as those sold under trade name PECEOL™), glyceryl monolinoleate (such as those sold under trade name MAISINE™ 35-1), medium-chain triglycerides, polyglyceryl oleate (such as those sold under trade name PLUROL OLEIQUE™ CC497), lauroyl polyoxylglyceride (such as those sold under trade name GELUCIRE™ 44/14), stearoyl polyoxylglycerides (such as those sold under trade name GELUCIRE™ 50/13), propylene glycol dicaprylocaprate (such as those sold under trade name LABRAFAC™ PG), propylene glycol laurate (such as those sold under trade name LAUROGLYCOL™ FCC), propylene glycol monolaurate (such as those sold under trade name LAUROGLYCOL™ 90), propylene glycol caprylate (such as those sold under trade name CAPRYOL™ PGMC) and propylene glycol monocaprylate (such as those sold under trade name CAPRYOL™ 90). These surfactants can be used alone or in combination, subject to the HLB characteristic described herein. More preferably, surfactant(s) having a HLB value from about 9 to about 13, ever more preferably from about 10 to about 12, is included in the SEP composition. For example, the SEP composition can include a mixture of polysorbate and oleoyl polyoxylglycerides as the surfactant system. The precise identity and amount of the surfactant system are not critical, but the system is preferably present in an amount of from about 20% to about 75% (w/w) based on the weight of the SEP composition.

The SEP composition includes one or more hydrophilic carriers that are compatible with the GEM-solvent solution and the surfactant system. As used herein "compatible" means that the hydrophilic carrier(s) can be mixed or dispersed with the GEM-solvent solution and the surfactant system so as to form a stable homogenous solution without extensive mixing or other processing. Preferably, each hydrophilic carrier is combinable with the other components of the SEP composition in amounts such that 1 part of GEM or a GEM salt is homogenously combined with about 10 to 10,000 parts (by weight) of the hydrophilic carrier. Examples of suitable hydrophilic carriers include polysorbate, ethanol, polyethylene glycols (PEGs, such as PEG200, PEG300, PEG400, PEG600, PEG1000, PEG2000, PEG3000, PEG4000, PEG6000, or PEG8000), glycerol, 1,2-propanediol (propylene glycol), propylene carbonate (PC), and diethylene glycol monoethyl ether (such as that sold under the trade name TRANSCUTOL™ HP). The hydrophilic carrier(s) is preferably present in an amount from about 2% to about 60% (w/w) based on the weight of the SEP composition.

The SEP composition can, optionally, include other components, such as an antioxidant (e.g. D-α-tocopheryl polyethylene glycol 1000 succinate, TPGS). The pH of the SEP composition is preferably adjusted to have a pH above the dissociation constant (pKa) of GEM (i.e., abouve pH 4.0), such as a pH of 5-8.

The components and amounts of the SEP composition should be selected (e.g., empirically) to exhibit good stability during storage, which particularly means that there is no substantial phase separation, material precipitation, texture change, or degradation of GEM contained therein during a selected storage period, such as a period of one, three, six, or twelve months. "No substantial degradation of GEM" means that the amount of GEM which becomes therapeutically inactive in the composition after being stored for the selected period of time is less than about 20%, and preferably less than about 10%, of the original amount.

In some embodiments, the solvent(s) and the hydrophilic carrier(s) are particularly together present in an amount ranging from about 25% to about 65% (w/w), more particularly about 40% to about 60% (w/w), and even more particularly about 50% (w/w), based on the weight of the pharmaceutical composition of the invention. Specifically, the solvent(s) and the hydrophilic carrier(s) are present at the ratio of about 1:0.1 to about 1:9 by weight in the pharmaceutical composition of the invention. More specifically, if the pharmaceutical composition of the invention is in the form of oral solution, the solvent(s) and the hydrophilic carrier(s) are present at the ratio of about 1:0.1 to about 1:2 by weight in the pharmaceutical composition of the invention; and if the pharmaceutical composition of the invention is in the form of capsule, the solvent(s) and the hydrophilic carrier(s) are present at the ratio of about 1:1 to about 1:9 by weight in the pharmaceutical composition of the invention. On the other hand, the hydrophilic carrier(s) and the surfactant system are particularly together present in an amount ranging from about 50% to about 95% (w/w), more particularly about 65% to about 85% (w/w), and even more particularly about 75% (w/w), based on the weight of the pharmaceutical composition of the invention. Specifically, the hydrophilic carrier(s) and the surfactant system are present at the ratio of about 1:0.3 to about 1:32.5, more specifically about 1:1 to about 1:20, and even more specifically about 1:1.5 by weight in the pharmaceutical composition of the invention.

In one embodiment, the solvent(s), the hydrophilic carrier (s) and the surfactant system are present at the ratio of about 2:3:4.5 by weight in the pharmaceutical composition of the invention.

In a certain embodiment, the self micro-emulsifying pharmaceutical composition of the invention comprises gemcitabine or its pharmaceutically acceptable salt, water, glycerol, PEG, polysorbate, and oleoyl polyoxylglycerides. In a specific example, gemcitabine is present in an amount of about 2.00% (w/w) based on the weight of the pharmaceutical composition; water is present in an amount of about 20.00% (w/w) based on the weight of the pharmaceutical composition; glycerol and PEG are together present in an amount of about 32.30% (w/w) based on the weight of the pharmaceutical composition; and polysorbate, and oleoyl polyoxylglycerides are together present in an amount of about 45.70% (w/w) based on the weight of the pharmaceutical composition.

In a certain embodiment, the self-emulsifying pharmaceutical composition of the invention comprises gemcitabine or its pharmaceutically acceptable salt, water, propylene glycol, PEG, polysorbate, and oleoyl polyoxylglycerides. In a specific example, gemcitabine is present in an amount of about 2.00% (w/w) based on the weight of the pharmaceutical composition; water is present in an amount of about 20.00% (w/w) based on the weight of the pharmaceutical composition; propylene glycol and PEG are together present in an amount of about 32.30% (w/w) based on the weight of the pharmaceutical composition; and polysorbate, and oleoyl polyoxylglycerides are together present in an amount of about 45.70% (w/w) based on the weight of the pharmaceutical composition.

In a certain embodiment, the self-emulsifying pharmaceutical composition of the invention comprises gemcitabine or its pharmaceutically acceptable salt, water, glycerol, PEG, polysorbate, oleoyl polyoxylglycerides, and TPGS. In a specific example, gemcitabine is present in an amount of about 1.98% (w/w) based on the weight of the pharmaceutical composition; water is present in an amount of about 19.8% (w/w) based on the weight of the pharmaceutical composition; glycerol and PEG are together present in an amount of about 31.98% (w/w) based on the weight of the pharmaceutical composition; polysorbate and oleoyl polyoxylglycerides are together present in an amount of about 45.25% (w/w) based on the weight of the pharmaceutical composition; and TPGS is present in an amount of about 0.99% (w/w) based on the weight of the pharmaceutical composition.

Pharmaceutical compositions of this invention may be orally administered in any orally acceptable dosage form including, but not limited to, capsules, tablets, powders or coated granules, which may contain pharmaceutical excipients known in the art such as binders, fillers, filler/binders, adsorbents, moistening agents, disintegrants, lubricants and the like as needed.

In certain embodiments of the invention, the pharmaceutical composition is encapsulated in a sealed soft or hard capsule. The capsule can be of any known kind which dissolves in a particular region of the GI tract, for example, releasing its content there. An example of such a capsule is an enteric-coated soft or hard gelatin capsule. Enteric coating, as known, is coating with a substance or a combination of substances that resists dissolution in gastric fluid but disintegrates in the intestine.

The SEP composition described herein can be prepared by mixing GEM with the one or more solvents, the one or more hydrophilic carriers, and the surfactant system using any standard method commonly used in the art in view of the present disclosure. In some embodiments, GEM is mixed with the one or more solvents and the one or more hydrophilic carriers first and then further mixed with the surfactant system. Details of the preparation are described in the examples below.

SEP compositions of GEM are described in U.S. patent application publication number 2010/0273730 of Innopharmax, Inc. (see, e.g., "Formulation IV" in that publication), and these formulations, adjusted to deliver metronomic dosage amounts, can be used in the methods described herein.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

The following abbreviations are used in the examples:
"GEM" means gemcitabine.
"5FU" means 5-fluorouracil.
"Q3D" has its traditional meaning of every three days.
"Q2D" has its traditional meaning of every two days.
"GEMORAL" means a self-emulsifying preparation of GEM formulated for oral administration, as described herein.

Example 1

GEMORAL Preparation

The GEMORAL composition described herein had the following composition, expressed as amounts per unit dose for a formulation intended to contain 80 mg of GEM free base per unit dose.

| Material | Amount Per Unit Dose (mg) | Percentage (%) |
|---|---|---|
| Gemcitabine Hydrochloride | 91.36 | 2.00 |
| Glycerin, USP | 95.92 | 2.10 |

-continued

| Material | Amount Per Unit Dose (mg) | Percentage (%) |
|---|---|---|
| TWEEN ® 80 (surfactant) | 1473.57 | 32.30 |
| PEG400 (polyethylene glycol) | 1379.48 | 30.20 |
| LABRAFIL ® M 1944 CS (surfactant) | 613.91 | 13.40 |
| Water, USP sterile for injection | 913.56 | 20.00 |
| Total | 4567.8 | 100.00 |

The GEMORAL composition described herein was made as follows. Glycerin and PEG400 were weighed out and mixed in an open-top container sufficiently that a visible vortex formed at the liquid surface. Mixing continued at least until the components were no longer separately distinguishable. To this solution, the indicated amount of GEM HCl was gradually added to the glycerin/PEG400 mixture, while mixing continued, over the course of about five minutes, and mixing continued for at least about 15 minutes after addition. While mixing continued, the pH of the mixture was adjusted to 6.00±0.10 by addition of 5N NaOH. The water was added to the mixture while stirring continued. Stirring continued for an additional ten minutes and was then discontinued. All steps to this point were performed at room temperature (about 20 degrees Celsius) using reagents which were at about room temperature, without imposed temperature control.

LABRAFIL® and TWEEN® 80 (surfactants) were combined and mixed to apparent homogeneity at 30 degrees Celsius sufficiently that a visible vortex formed at the liquid surface. While mixing continued, the GEM HCl-containing mixture was combined with the surfactant mixture, and mixing continued for about 30 minutes while the temperatures of the mixture was controlled at 30 degrees Celsius, and then mixing ceased and the combined mixture (the GEMORAL composition) was packaged (e.g., in vials) and stored (e.g., at 20-25 degrees Celsius).

For some experiments, the GEMORAL composition was packaged and stored in individual vials, each of which contained about 4.6 grams of GEMORAL composition. For other experiments, larger quantities of the GEMORAL composition were stored in bulk before use. The GEMORAL formulation is suitable for inclusion in various dosage forms, including soft-gel type capsules. For example, an amount of the GEMORAL formulation that contains 40 mg of GEM (on a free base basis) can be incorporated alone, or mixed with other excipients, into a soft-gel capsule for oral administration.

To make the dosing solution (1 and 0.3 mg/ml GEM on a free base basis) used in xenografted mouse studies described herein, the GEMORAL formulation described above was brought to room temperature (about 25 degrees Celsius), combined with deionized water under stirring at room temperature To make a 10 mg/kg GEM oral dosing solution, 6.289 grams of a 1.6 mg/kg GEMORAL solution (made by diluting 80 mg of GEMORAL formulation with deionized water to yield a composition containing 1.6 mg/ml GEM on a free-base basis) was combined with water in a 10 milliliter volumetric flask. Following stirring, the volume was brought to 10.0 milliliters (to yield a 1 mg GEM/ml solution) and the solution was administered orally to individual xenografted mice based on individual mouse body weight within four hours of preparation.

To make a 3 mg/kg GEM oral dosing solution, 1.887 grams of the 1.6 mg/kg GEMORAL solution was combined with water in a 10 milliliter volumetric flask. Following stirring, the volume was brought to 10.0 milliliters (to yield a 0.3 mg GEM/ml solution) and the solution was administered orally to individual xenografted mice based on individual mouse body weight within four hours of preparation.

Example 2

In Vivo Efficacy of High Dose GEM Injection and/or GEMORAL Administration in a Xenografted Mouse Model of Human Cholangiocarcinoma.

This example describes a study in which the effects of gemcitabine upon mice into which portions of a human patient-derived cholangiocarcinoma were xenografted. The xenografted mice were then treated with one of five treatment regimens and the results observed.

To prepare the xenografted mice used in the study, primary human cholangiocarcinoma fragments obtained from human patients were injected into "stock" male BALB/c nude mice. Subsequently, tumor fragments (roughly 2-3 millimeters in diameter) were harvested from the "stock" mice and inoculated subcutaneously into the right flank of other male BALB/c nude mice. Tumor development in the inoculated mice was then observed, and 40 such mice were selected for inclusion in the study when their tumor volume reached about 180 cubic millimeters (volume was assessed by multiplying tumor length by ½ (tumor width squared) (i.e., $L \times W^2/2$), length and width being measured using a caliper). The mice were divided into 5 groups of 8 mice each for the study, all mice in each group having tumors of approximately equal size. The day on which mice were first dosed was designated "Day 1" of the study, and the study continued for 76 days. The mice were divided into Groups 1, 2, 3, 4, and 5. Mice of each group were treated identically.

Mice of Group 1 were intraperitoneally injected with 60 mg/kg of GEM on days 1, 4, 7, and 10 of the study (i.e., Q3D×4) and were not further treated thereafter.

Mice of Group 2 were intraperitoneally injected with 60 mg/kg of GEM on days 1, 4, 7, and 10 of the study (i.e., Q3D×4). Beginning on day 13 of the study, the mice were orally administered 10 mg/kg GEM in the GEMORAL composition (hereinafter "10 mg/kg GEMORAL") every other day (i.e., Q2D×32) through the end of the study.

Mice of Group 3 were intraperitoneally injected with 60 mg/kg of GEM on days 1, 4, 7, and 10 of the study (i.e., Q3D×4). Also beginning on day 1 of the study, the mice were orally administered 10 mg/kg GEMORAL every other day (i.e., Q2D×38) through the end of the study.

Mice of Group 4 were orally administered 10 mg/kg GEMORAL every other day (i.e., Q2D×38), beginning on day 1 of the study and extending through the end of the study.

Mice of Group 5 were controls and were not administered GEM. They were intraperitoneally injected with saline on days 1, 4, 7, and 10 of the study (i.e., Q3D×4). Beginning on day 13 of the study, the mice were orally administered distilled, deionized water every other day (i.e., Q2D×32) through the end of the study.

Figure 2:
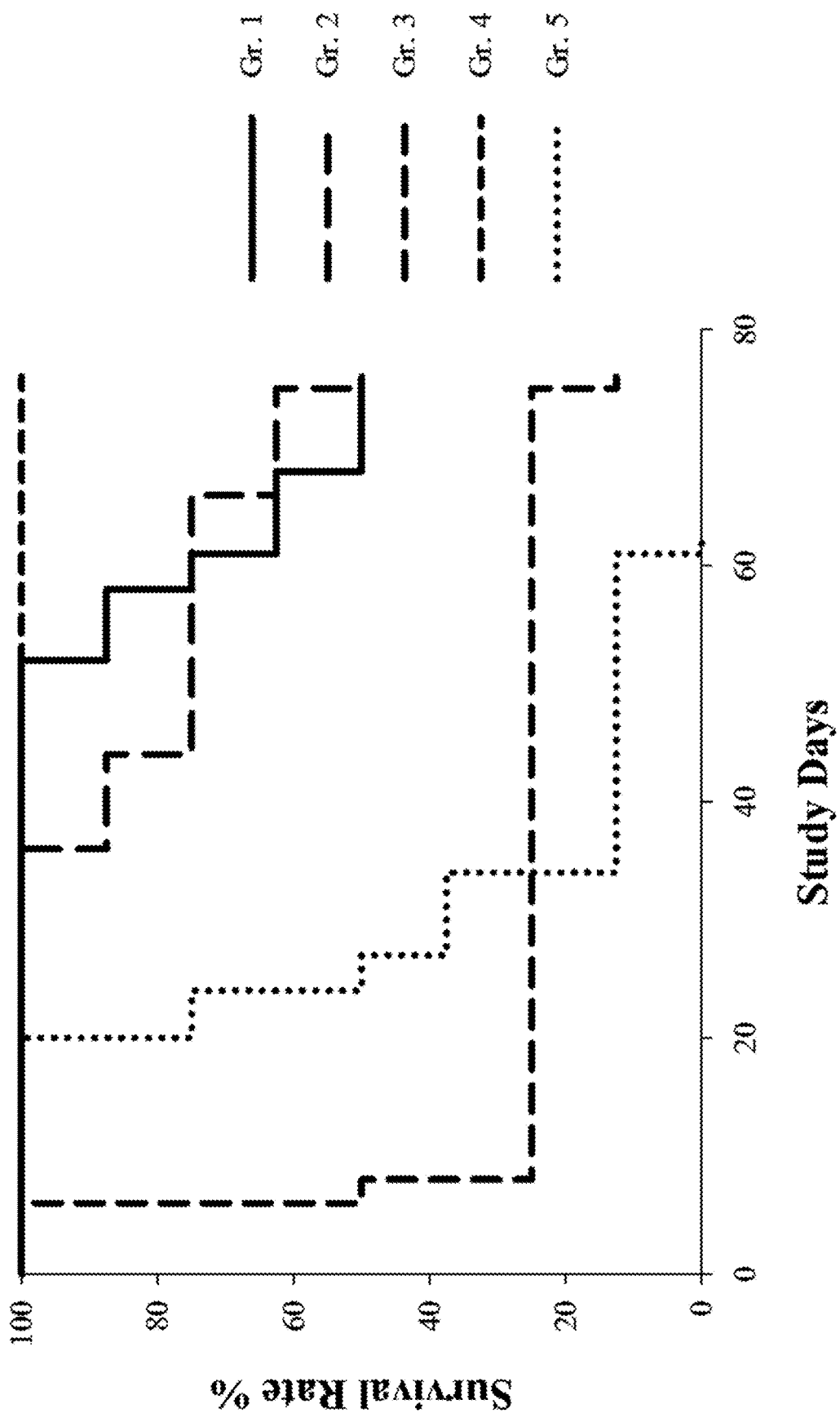
FIG. 2 is a graph of survival rate for animals of the study described in Example 2.

The study was continued until day 76 and the body weight losses among the mice of the various Groups were observed. For each of Groups 1 and 2, 4 of 8 mice were dead by day 76 ("dead" included both mice which had died and mice exhibiting tumor size >1000 cubic millimeters). Survival rates of mice used in the study are shown in FIG. 2. For Group 3, 6 of 8 mice were dead by day 10. For Group 4, treatment was well tolerated, as evidenced by the fact that all mice survived until day 76 (in the control Group 5, by contrast, all mice died by about day 62).

As illustrated in FIG. 1, mice from each of Groups 1, 2, 3, and 4 exhibited significant tumor regression (i.e., anti-tumor response), compared with the control mice of Group 5.

The effects of the various treatments on tumor volume are shown in FIG. 1. Compared with vehicle group (Group 5), mice of Groups 1, 2, 3, and 4 exhibited significant anti-tumor responses. Values reflecting anti-tumor responses, as compared with vehicle treatment (T/C %, calculated as the ratio of average tumor volume in treatment group vs. average tumor volume in the control group {Group 5}, expressed as a percentage) on different study days are indicated in Table 1. Group 1 mice (i.e., MTD of GEM, 60 mg/kg Q3D×4; cumulative dose=240 mg/kg), exhibited a significant anti-tumor response (T/C=52%) on day 14. Mice of Groups 2 and 4 exhibited similar responses (T/C values of 58% and 57%) on day 14; it is noteworthy that by day 14 the cumulative dose of GEM for Group 4 was only about 25% that of Group 1.

Animals in Group 1 exhibited significant tumor growth after completing the scheduled dosing (i.e. after day 11) in group 1. In contrast, animals of Groups 2 and 4 exhibited smaller tumor volume from day 42 to 76 than the original tumor volume on day 0. GEMORAL as single agent or following GEM-MTD treatment, produced significant anti-tumor response as compared with vehicle treatment (T/C=3% for each of Groups 2 and 4, P<0.05 on day 76). Moreover, tumor volume in Groups 2 and 4 demonstrated significantly greater tumor growth inhibition than an MTD schedule (Group 1) from day 42 to 76 (p<0.05).

TABLE 1

Anti-Tumor Response of Treatments vs. Patient-Derived Cholangiocarcinoma Xenografts.

| Group | Day 14 | | Day 42 | | Day 73 | | Day 76 | |
|---|---|---|---|---|---|---|---|---|
| | T/C, % | P | T/C, % | P | T/C, % | P | T/C, % | P |
| 1 | 52 | <0.001 | 22 | 0.002 | 46 | 0.018 | 49 | 0.022 |
| 2 | 58 | 0.001 | 10 | 0.001 | 3 | 0.001 | 3 | 0.001 |
| 3 | 31 | 0.002 | 7 | 0.025 | 1 | 0.007 | 3 | — |
| 4 | 57 | 0.004 | 8 | 0.001 | 3 | 0.001 | 3 | 0.001 |
| 5 | — | — | — | — | — | — | — | — |

Tumor-xenografted mice which received GEMORAL in addition to injected GEM (Groups 2 and 3), or which received GEMORAL alone (Group 4), exhibited greater tumor regression than mice which received injected GEM alone (Group 1). Mice which received both oral and injected gemcitabine during the first ten days of the study exhibited greater mortality than those which received only injected drug (a potential drug toxicity effect). Mice which received only oral gemcitabine exhibited lower mortality than those which received only injected or both oral and injected drug, until the very end of the study.

These results indicate that oral metronomic gemcitabine can be effectively used, together with injected gemcitabine, or without injected gemcitabine to induce regression of at least cholangiocarcinomas.

Example 3

In Vivo Efficacy of High Dose GEM Injection and/or GEMORAL Administration in a Second Xenografted Mouse Model of Human Cholangiocarcinoma.

Example 3 is a study in which the effects of GEM upon mice into which cells of human cholangiocarcinoma cell line HuCCT1 were xenografted. The xenografted mice were then treated with one of five treatment regimens and the results observed over the study period of 90 days.

To prepare the xenografted mice used in the study, $1 \times 10^6$ HuCCT1 human cholangiocarcinoma cells were were transplanted subcutaneously on the right flank of 6 week old male BALB/c nude mice. Tumor growth was observed once a week and the tumor volume was measured as $L \times W^2/2$ by caliper. Tumor development in the xenografted mice was then observed, and 40 such mice were selected for inclusion in the study when their tumor volume reached about 124 cubic millimeters. The mice were divided into 5 groups of 8 mice each for the study. The day on which mice were first dosed was designated "Day 0" of the study, and the study continued for 90 days.

Mice of Group 1 were intraperitoneally injected with 60 mg/kg of GEM on days 0, 3, 6, and 9 of the study (i.e., Q3D×4) and were not further treated thereafter.

Mice of Group 2 were intraperitoneally injected with 60 mg/kg of GEM on days 0, 3, 6, and 9 of the study (i.e., Q3D×4). Beginning on day 13 of the study, the mice were orally administered 10 mg/kg GEM in the GEMORAL composition (hereinafter "10 mg/kg GEMORAL") every other day (i.e., Q2D×40) through the end of the study.

Mice of Group 3 were intraperitoneally injected with 60 mg/kg of GEM on days 0, 3, 6, and 9 of the study (i.e., Q3D×4). Also beginning on day 1 of the study, the mice were orally administered 10 mg/kg GEMORAL every other day (i.e., Q2D×46) through the end of the study.

Mice of Group 4 were orally administered 10 mg/kg GEMORAL every other day (i.e., Q2D×46), beginning on day 1 of the study and extending through the end of the study.

Mice of Group 5 were controls and were not administered GEM. They were intraperitoneally injected with saline on days 0, 3, 6, and 9 of the study (i.e., Q3D×4). Beginning on day 13 of the study, the mice were orally administered distilled, deionized water every other day (i.e., Q2D×40) through the end of the study.

Figure 4:
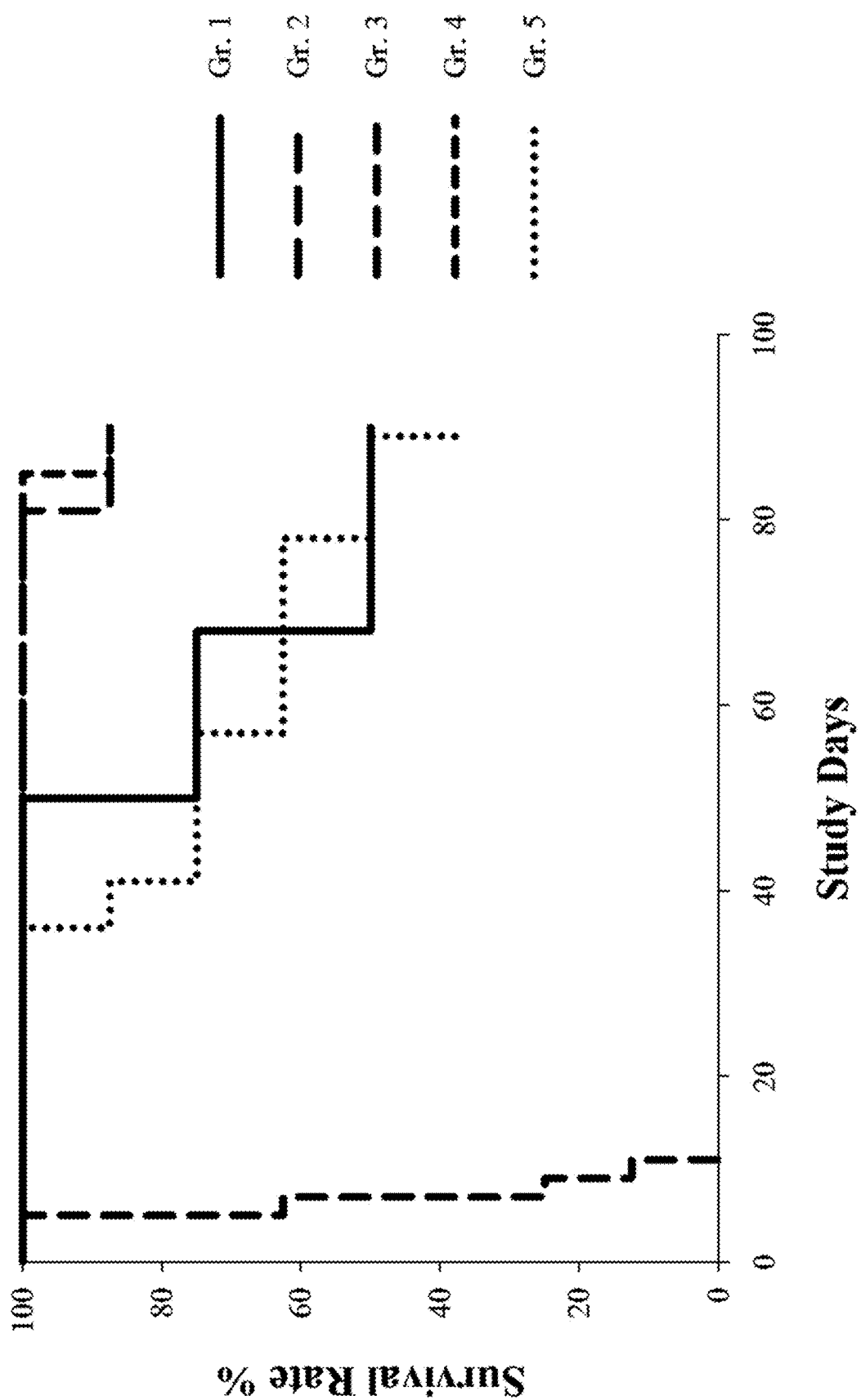
FIG. 4 is a graph of survival rate for animals of the study described in Example 3.

The study was continued until day 90 and body weight losses among the mice of the various Groups were observed. In Group 3, all mice lost over 20% body weight by day 12. Treatment was tolerated in all other treatment groups (i.e., Groups 1, 2, and 4, as indicated by the survival rates shown in FIG. 4. Survival rate were calculated using Kaplan-Maier analysis and the survival rates at day 90 were 50% (4/8 mice) for Group 1, 87.5% (7/8 mice) for Group 2, 0% (0/8 mice) for Group 3, 87.5% (7/8 mice) for Group 4, and 37.5% (3/8 mice) for Group 5. The mean survival time (MST) for mice in Group 1, 2, 3, 4 and 5 were 69, >90, 8, >90 and 79 days, respectively. The MSTs for mice in Groups 2 and 4 were marginally significantly prolonged as compared with the vehicle treatment (Group 5). MST was not significantly different among mice in Group 1, 3 and 5.

Figure 3:
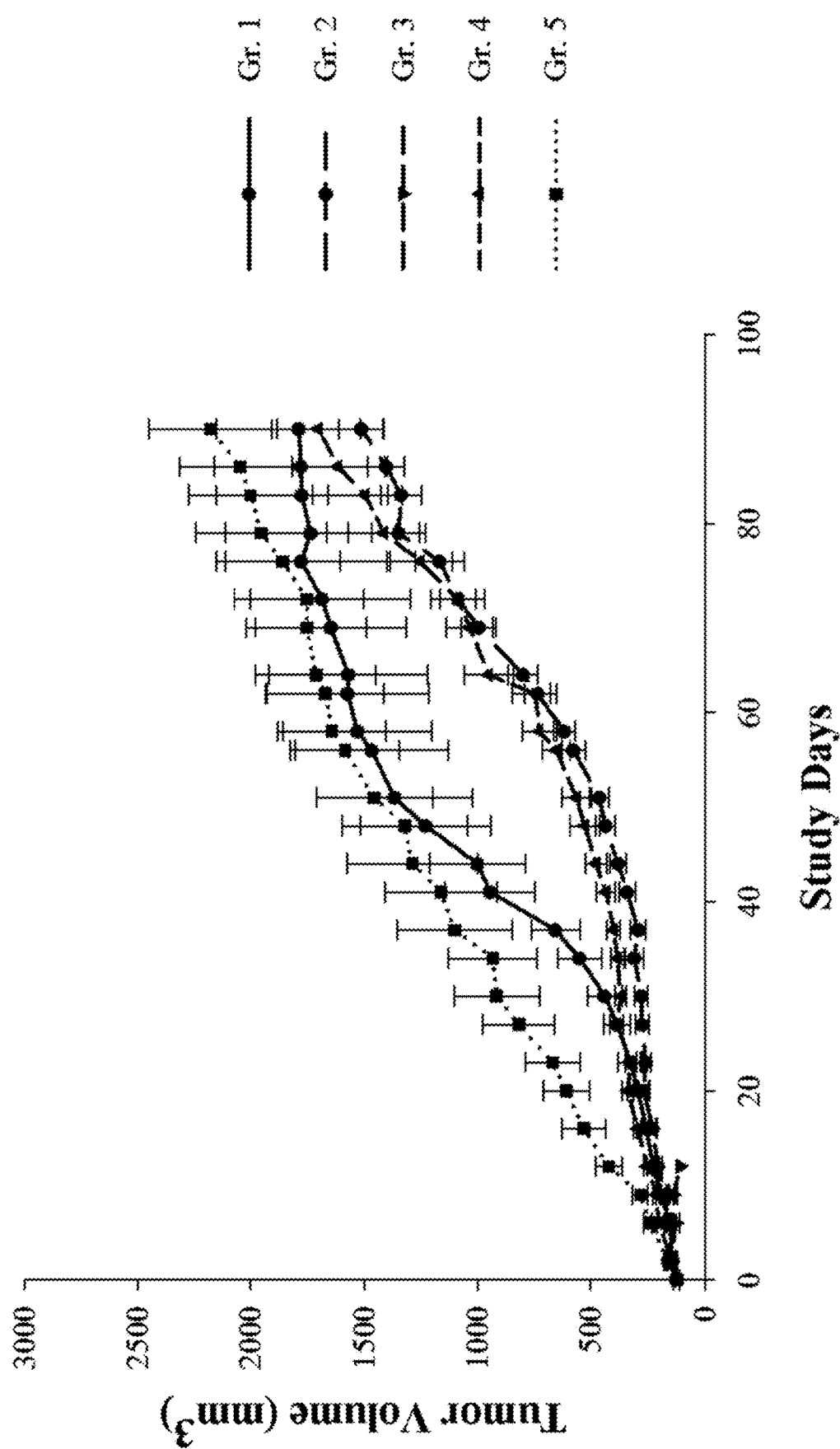
FIG. 3 is a graph of tumor volume over time for animals to which the human cholangiocarcinoma cell line HuCCT1 had been xenografted. Further details are described in Example 3.

As illustrated in FIG. 3, mice from each of Groups 1, 2, 3, and 4 exhibited significant tumor regression (i.e., anti-tumor response), compared with the control mice of Group 5. Values reflecting anti-tumor responses, as compared with vehicle treatment (T/C %) on different study days are indicated in Table 2. Mice of Groups 1, 2, and 4 exhibited significant anti-tumor responses from day 6 to day 30, from day 6 to day 90, and from day 12 to day 76, respectively, and the maximum tumor growth inhibition values were 47% on day 27 for Group 1, 27% on day 37 for Group 2, and 36% on day 37 for Group 4. It is noteworthy that by day 12 the cumulative dose of GEM for Group 4 was only about 25% that of Group 1.

TABLE 2

Anti-Tumor Response of Treatments vs. HuCCT1 Cholangiocarcinoma Xenografts.

| Group | Day 12 | | Day 37 | | Day 58 | | Day 76 | | Day 90 | |
|---|---|---|---|---|---|---|---|---|---|---|
| | T/C, % | P | T/C, % | P | T/C, % | P | T/C, % | P | T/C, % | P |
| 1 | 54 | 0.013 | 60 | 0.129 | 93 | 0.789 | 96 | 0.864 | 82 | 0.422 |
| 2 | 49 | 0.008 | 27 | 0.007 | 38 | <0.001 | 63 | 0.017 | 70 | 0.032 |
| 3 | 28 | 0.038 | 18 | — | 24 | — | 46 | — | 59 | — |
| 4 | 60 | 0.024 | 36 | 0.0158 | 44 | 0.001 | 67 | 0.043 | 86 | 0.155 |
| 5 | — | — | — | — | — | — | — | — | — | — |

In this study, we found intraperitoneal injection of GEM at about the MTD could significantly inhibit cholangiocarcinoma tumor growth in vivo, whether or not a metronomic oral dose of GEM was administered together with or following injection; the oral metronomic GEM could also significantly inhibit cholangiocarcinoma tumor growth in vivo in the absence of GEM injection. However, GEM injection did not continue to exhibit significant anti-tumor activity after the GEM injections were ceased, as indicated in tumor growth observed in mice of Group 1 after day 30. Tumor relapse is known to follow clinical chemotherapy, at least sometimes, and these data appear to reflect that experience. We evaluated whether oral metronomic GEM combined with parenteral GEM therapy could repress the tumor growth for a longer period of time. The results indicate that oral metronomic GEM combined with parenteral GEM therapy significant extended tumor growth inhibition, relative to injected GEM monotherapy from at least day 34 to 58. Moreover, oral metronomic GEM monotherapy (i.e., Group 4) or when following parenteral GEM therapy (i.e., Group 2) produced significant anti-tumor activity as compared with vehicle treatment until at least day 76 and day 90, respectively. In addition, oral metronomic GEM monotherapy, either as monotherapy or following parenteral GEM therapy, significantly prolonged survival time as compared with vehicle treatment.

In summary, the results shown in this example indicate that oral metronomic GEM monotherapy, either as monotherapy or following parenteral GEM therapy inhibited HuCCT1 cholangiocarcinoma tumor growth and prolonged survival time in vivo, suggesting that these therapies may provide a new approach for treating at least cholangiocarcinomas and other tumors susceptible to GEM.

Example 4

In Vivo Efficacy of High Dose GEM Injection and/or GEMORAL Administration in a Xenografted Mouse Model of Human Pancreatic Cancer.

Example 4 is a study in which the effects of GEM upon mice into which cells of human pancreatic cancer cell line CFPAC-1 were xenografted. The xenografted mice were then treated with one of six treatment regimens and the results observed over the study period of 91 days.

To prepare the xenografted mice used in the study, $1 \times 10^6$ human CFPAC-1 pancreatic cancer cells were were transplanted subcutaneously on the right flank of 6 week old male BALB/c nude mice. Tumor growth was observed once a week and the tumor volume was measured as $L \times W^2/2$ by caliper. Tumor development in the xenografted mice was then observed, and 48 such mice were selected for inclusion in the study when their tumor volume reached about 141 cubic millimeters. The mice were divided into 6 groups of 8 mice each for the study. The day on which mice were first dosed was designated "Day 0" of the study, and the study continued for 91 days.

Mice of Group 1 were intraperitoneally injected with 120 mg/kg of GEM on day 0 and every third day thereafter through day 66 (i.e., Q3D×23) and were not further treated thereafter.

Mice of Group 2 were intraperitoneally injected with 120 mg/kg of GEM on days 0, 3, 6, and 9 of the study (i.e., Q3D×4). Beginning on day 12 of the study, the mice were orally administered 10 mg/kg GEM in the GEMORAL composition (hereinafter "10 mg/kg GEMORAL") every other day (i.e., Q2D×28) through day 66; the mice were not further treated thereafter.

Mice of Group 3 were intraperitoneally injected with 120 mg/kg of GEM on days 0, 3, 6, and 9 of the study (i.e., Q3D×4). Beginning on day 12 of the study, the mice were orally administered 3 mg/kg GEM in the GEMORAL composition (hereinafter "3 mg/kg GEMORAL") every day (i.e., QD×55) through day 66; the mice were not further treated thereafter.

Mice of Group 4 were orally administered 3 mg/kg GEMORAL every day (i.e., QD×92), beginning on day 0 of the study and extending through the end of the study.

Mice of Group 5 were orally administered 10 mg/kg GEMORAL every other day (i.e., Q2D×46), beginning on day 0 of the study and extending through the end of the study.

Mice of Group 6 were controls and were not administered GEM. They were intraperitoneally injected with saline on days 0, 3, 6, and 9 of the study (i.e., Q3D×4). Beginning on day 13 of the study, the mice were orally administered distilled, deionized water every other day (i.e., Q2D×28) through the end of the study.

Figure 6:
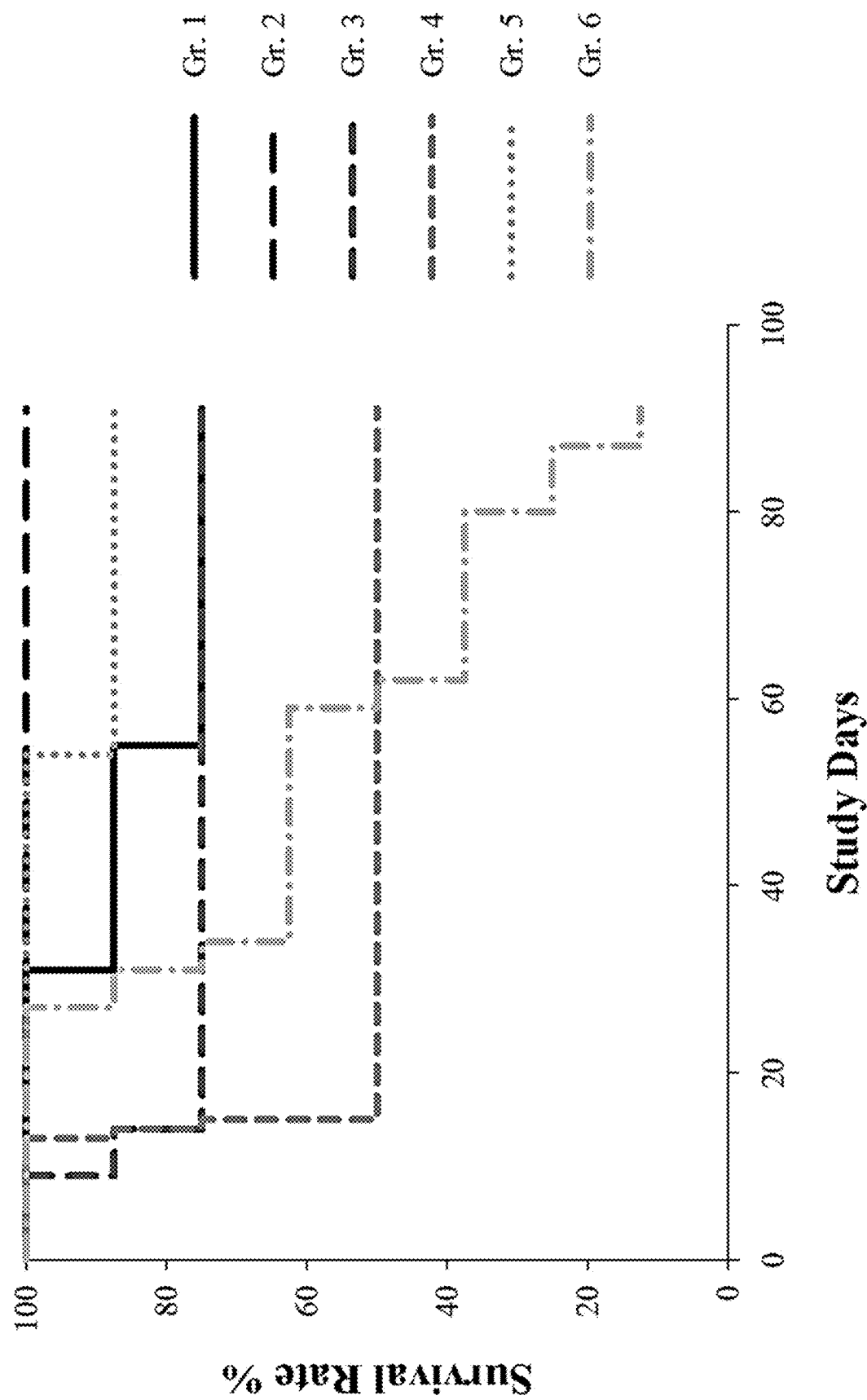
FIG. 6 is a graph of survival rate for animals of the study described in Example 4.

The study was continued until day 91. Survival rates of mice used in the study are shown in FIG. 6. Survival rates were evaluated using a Kaplan-Maier analysis ("dead" included both mice which had died and mice exhibiting tumor size >2500 cubic millimeters). The MSTs for mice in Groups 1, 2, 3, 4, 5, and 6 were >91, >91, >91, 53.5, >91, and 60 days, respectively. The MSTs for mice in Groups 1, 2, 3 and 5 were marginally significantly prolonged as compared with the vehicle treatment (Group 6). MST was not significantly different between mice in Group 4 and vehicle group (Group 6).

Figure 5:
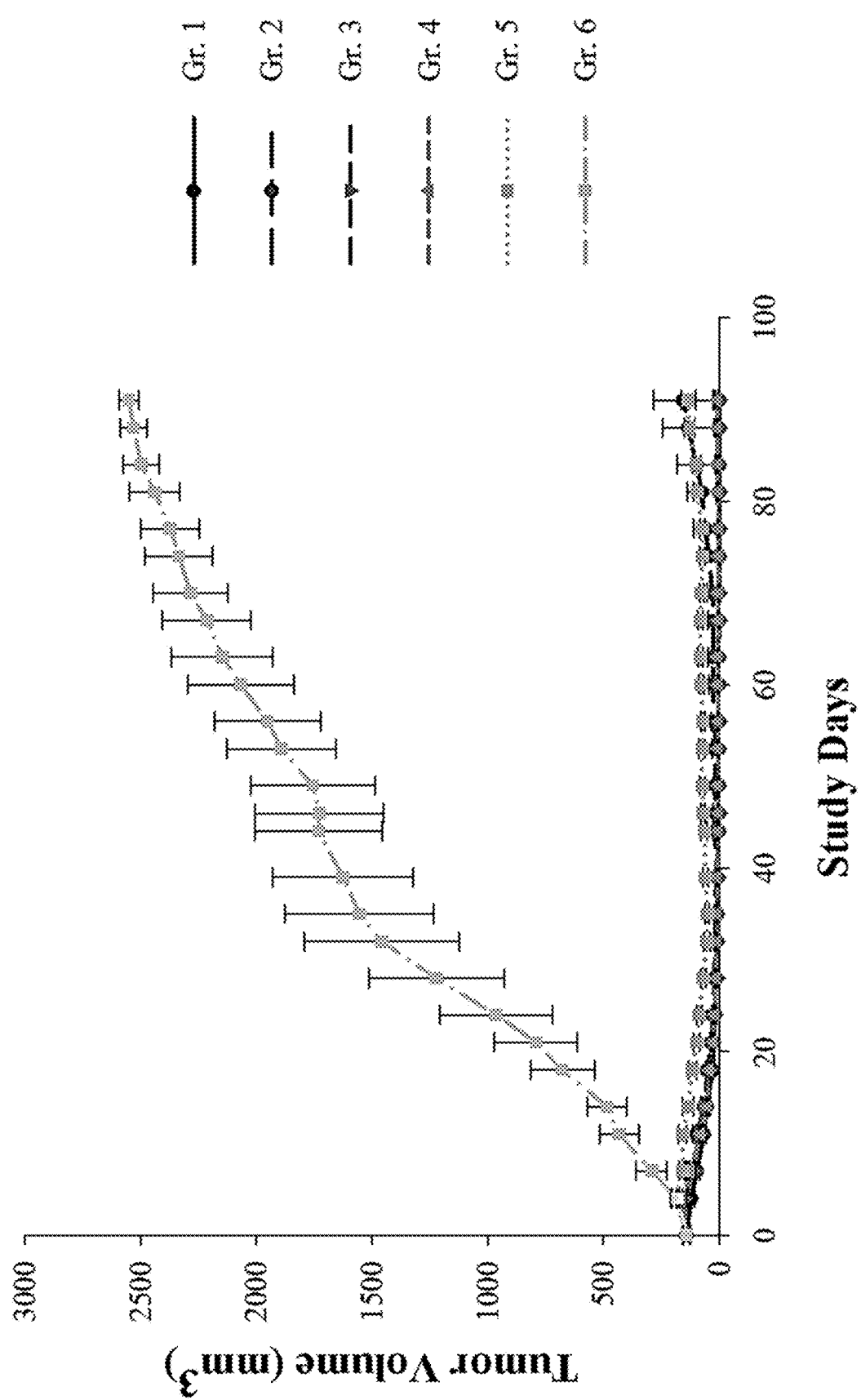
FIG. 5 is a graph of tumor volume over time for animals to which the human pancreatic cancer cell line CFPAC-1 had been xenografted. Further details are described in Example 4.

Tumor growth for mice in each Group is shown in FIG. 5. Mice in each of Groups 1, 2, 3, 4 and 5 exhibited significant anti-tumor response from day 14 to 91 as compared with vehicle treatment (Group 6). Maximum anti-tumor response was observed on day 81 (T/C 0%) for mice of Group 1, on day 39 (T/C 0.8%) for mice of Group 2, on day 67 (T/C 0%) for mice of Group 3, on day 74 (T/C 0.1%) for mice of Group 4, and on day 77 (T/C 3%) for mice of Group 5. Moreover, compared with tumor volume in mice in the vehicle treatment group (Group 6), mice in each treatment group exhibited tumor regression after 1-2 weeks of treatment. At least some mice in several treatment groups were tumor free—at days 44-91 for mice of Group 1 (6/8 mice tumor free at day 91), at days 32-91 for mice of Group 2 (6/8 mice tumor free at day 91), at days 28-91 for mice of Group 3 (5/8 mice tumor free at day 91), and at days 39-91 for mice of Group 4 (2/8 mice tumor free at day 91).

Some mice showed partial response rate, meaning that at least a 30% decrease in tumor volume (relative to parental tumor volume) was observed. Proportions of such mice were 13% (1/8 mice) in Group 3, 25% (2/8 mice) in Group 4, and 38% (3/8 mice) in Group 5.

In this study, we found that oral metronomic administration of GEM, intraperitoneal injection of near-MTD GEM, and combinations of these therapies exhibit in vivo efficacy against a human pancreatic cancer cell line xenografted into mice. These data indicate that these treatments can be used to treat pancreatic cancers in humans.

Example 5

In Vivo Efficacy of 5-Fluorouracil Injection Followed by GEMORAL Administration in a Xenografted Mouse Model of Human Pancreatic Cancer.

Pancreatic cancer monotherapy using 5-fluorouracil (5FU) injection is known. However, some pancreatic tumors do not respond (or do no respond strongly) to 5FU therapy. We investigated oral metronomic GEM administration as a second-line treatment in 5FU-non-responsive pancreatic tumors using a xenograft model.

To prepare the xenografted mice used in the study, $1 \times 10^6$ human CFPAC-1 pancreatic cancer cells were were transplanted subcutaneously on the right flank of 6 week old male BALB/c nude mice. Tumor growth was observed once a week, tumor volume was measured as $L \times W^2/2$ by caliper, and mice were selected for inclusion in the study when their tumor volume reached about 131 cubic millimeters. The mice were divided into four groups of 6-8 mice each for the study. The day on which mice were first dosed was designated "Day 0" of the study, and the study continued for 112 days.

Mice of Group 1 were orally administered 10 mg/kg GEMORAL every other day (i.e., Q2D×56), beginning on day 0 of the study and extending through the end of the study.

Mice of Group 2 were intraperitoneally injected thrice weekly with 20 mg/kg of 5FU beginning on day 0 and continuing for the first 9 weeks of the study. Beginning on day 63 of the study, the mice were orally administered 10 mg/kg GEMORAL every other day (i.e., Q2D×25) through the end of the study.

Mice of Group 3 were intraperitoneally injected thrice weekly with 20 mg/kg of 5FU beginning on day 0 and continuing for the first 3 weeks of the study. Beginning on day 21 of the study, the mice were orally administered 10 mg/kg GEMORAL every other day (i.e., Q2D×46) through the end of the study.

Mice of Group 4 were controls and were not administered 5FU or GEM. They were intraperitoneally injected with saline on days 0, 3, 6, and 9 of the study (i.e., Q3D×4). Beginning on day 13 of the study, the mice were orally administered distilled, deionized water every other day (i.e., Q2D×51) through the end of the study.

Figure 8:
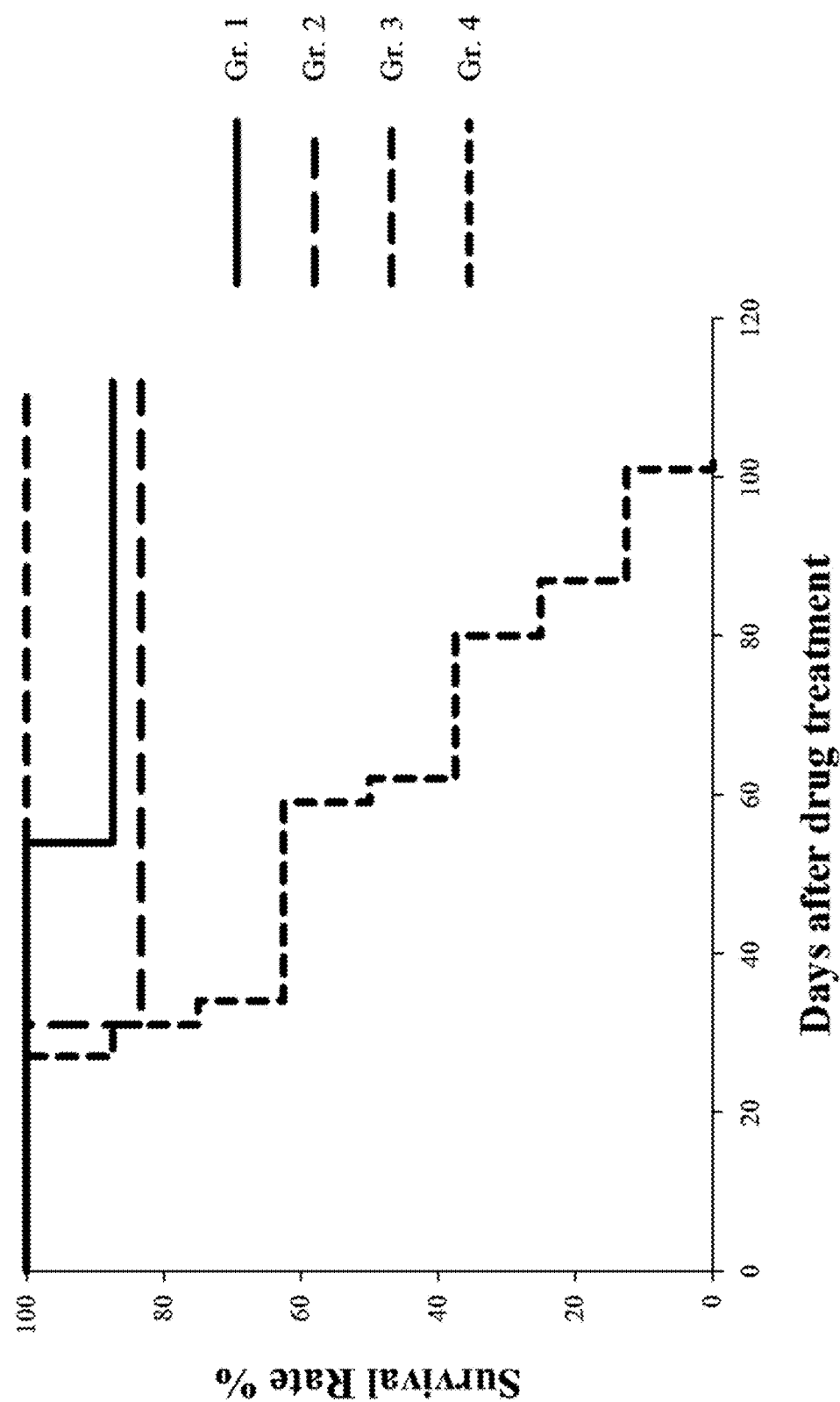
FIG. 8 is a graph of survival rate for animals of the study described in Example 5.

The study was continued until day 112. Survival rates of mice used in the study are shown in FIG. 8 and were evaluated using a Kaplan-Maier analysis ("dead" included both mice which had died and mice exhibiting tumor size >2500 cubic millimeters). The MSTs for mice in Groups 1, 2, 3, and 4 were >112, >112, >112, and 60 days, respectively. The MSTs for mice in Groups 1, 2, and 3 were marginally significantly prolonged as compared with the vehicle treatment (Group 4).

Figure 7:
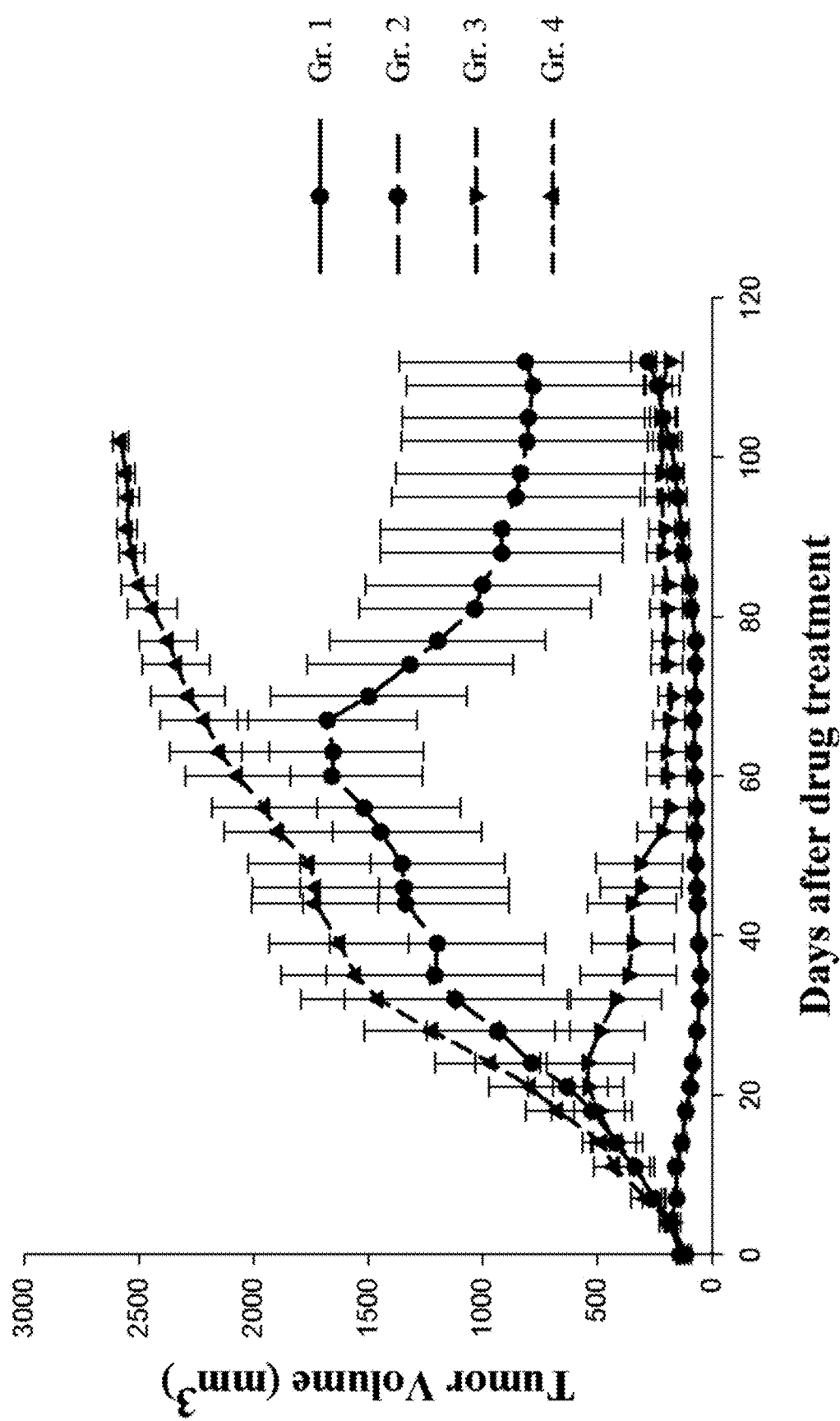
FIG. 7 is a graph of tumor volume over time for animals to which the human pancreatic cancer cell line CFPAC-1 had been xenografted. Further details are described in Example 5.

Tumor growth for mice in each Group is shown in FIG. 7. Mice in each of Groups 1, 2, and 3 exhibited significant anti-tumor responses as compared with vehicle treatment (Group 4), at days 11-112 for Group 1, at days 74-112 for Group 2, and at days 32-112 for Group 3. Maximum anti-tumor response was observed on day 77 (T/C 3%) for mice of Group 1, on day 105 (T/C 39%) for mice of Group 2, and on day 112 (T/C 8%) for mice of Group 3.

No significant anti-tumor response attributable to 5FU treatment was observed in the mice of Groups 2 and 3. However, anti-tumor response attributable to oral metronomic GEM was observable shortly after commencement of GEMORAL administration (with anti-tumor response significantly different than vehicle-treated mice beginning at least by day 74 for Group 2 and by day 32 for Group 3).

One mouse of Group 3 was tumor-free by day 112.

These results indicate that oral metronomic GEM administration can be used as a second-line treatment for 5FU-treated pancreatic cancers, or for primary treatment of such cancers that are not responsive to 5FU treatment.

Example 6

Determination of MTD for GEMORAL for Metronomic Dose Selection in Human Patients Dose escalation studies were performed in sequential cohorts of 3 to 6 human patients each (average body weights considered to be 60 kg) in an attempt to determine the MTD for GEM orally administered in the GEMORAL formulation. No DLT was observed for the GEMORAL over the dose range studied. These experiments demonstrate that the MTD for GEM orally administered in the GEMORAL formulation is greater than the 80 mg (1.33 mg/kg body weight) dose in the dosing schedule studied.

In a first phase of these studies, GEMORAL was orally administered to individual human patients at one of the doses 2, 5, 10, 20, 30, 40, 50, 60, 70, 80 mg GEM (expressed on a GEM free base basis), corresponding to doses of 0.033 mg/kg, 0.083 mg/kg, 0.17 mg/kg, 0.33 mg/kg, 0.50 mg/kg, 0.67 mg/kg, 0.83 mg/kg, 1.00 mg/kg, 1.17 mg/kg, 1.33 mg/kg body weight. The selected dose was orally administered to each patient on days 1, 3, 5, 8, 10, and 12 (i.e., 6 doses total) of a 21-day study cycle. In each cohort, the dosing regimen was well tolerated. No DLTs occurred in any patient for any of the dose cohorts. The MTD was therefore not identified, but it was determined that 80 mg is a safe dose for this dosing regimen.

An open label, multicenter study of GEMORAL following primary chemotherapy or combined chemoradiotherapy for advanced biliary tract cancer will be evaluated. This study will be conducted in 2 parts: a dose escalation phase (Part 1) and a dose expansion phase (Part 2).

In both Part 1 and Part 2, eligible patients will be assigned to be orally administered GEMORAL in softgel dosage form on days 1, 3, 5, 8, 10, 12, 15, 17, and 19 of a 21-day cycle (9 doses per cycle). There will be no gap between the cycles, i.e., the next cycle will commence immediately on the next day after day 21 of the previous cycle (i.e., day 22 overall for the second cycle), except that dosing on two consecutive days will not be allowed; there will be at least one day between doses.

Part 1: Dose Escalation Phase (Phase 1b)

Part 1 of the study will follow a 3+3 dose escalation scheme at predefined dose levels. There will be sequential cohorts of 3 to 6 patients each with increasing doses of 40 mg (0.67 mg/kg), 80 mg (1.33 mg/kg), and 120 mg (2.00 mg/kg) per cohort. There will be no intra-patient dose escalation. Cycle 1 (21 days) is defined as the dose limiting toxicity (DLT) assessment period. If an MTD is not identified following dose escalation to 120 mg (2.00 mg/kg), the intermediate dose level of 100 mg (1.67 mg/kg) may also be evaluated. If an intermediate dose level is evaluated, up to 6 additional patients will be enrolled at that dose level.

Part 2: Dose Expansion Phase (Phase 2)

The highest dose level of GEMORAL softgel dosage form tested at which fewer than two of the six patients in a cohort experience a DLT will be expanded in Part 2 of the study. In addition, because the highest dose level selected in Part 1 could lead to cumulative toxicity during treatment, the next lowest dose level below the highest evaluated in Part 1 at which at least two of six patients experienced a DLT will also be expanded for assessment in Part 2. If an MTD is not identified in Part 1 of the study, the two dose levels used in Part 2 will be 120 mg and 80 mg (2.00 and 1.33 mg/kg), or 120 mg and 100 mg (2.00 and 1.67 mg/kg) if the intermediate dose of 100 mg (1.67 mg/kg) has been evaluated in Part 1.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A method of treating a gemcitabine-sensitive tumor in a subject of a species, the method comprising
    orally administering to the subject a dosage form that comprises a therapeutically-effective amount of gemcitabine (GEM) or its pharmaceutically acceptable salt in a self-emulsifying formulation that, upon oral ingestion, releases in a bioavailable form less than half the maximum tolerated dose (MTD) of GEM for the species,
    wherein the formulation comprises (a) the GEM or its pharmaceutically acceptable salt dissolved in a hydrophilic solvent (b) a surfactant system that exhibits a hydrophilic-lipophilic balance (HLB) value of from about 8 to about 17 and that includes at least one surfactant; and (c) a hydrophilic carrier compatible with (a) and (b), and
    wherein the dosage form is administered to the subject multiple times on a regular schedule without a significant interruption for a sustained period of time.

2. The method of claim 1, wherein the formulation spontaneously forms an emulsion upon contacting an aqueous medium at 37 degrees Celsius under mild mechanical agitation.

3. The method of claim 1, wherein the formulation spontaneously forms an emulsion within the gastrointestinal tract of the subject.

4. The method of claim 3, wherein
    the hydrophilic solvent is selected from the group consisting of water, ethanol, polyethylene glycol (PEG), isopropanol (IPA), 1,2-propanediol (propylene glycol), glycerol, acetic acid, and combinations thereof;
    the surfactant system comprises one or more surfactant selected from the group consisting of polysorbate, poloxamers, oleoyl polyoxylglycerides, linoleoyl polyoxylglycerides, caprylocaproyl polyoxylglycerides, polyoxyethylene castor oil derivatives, polyoxyethylene alkyl ethers, sorbitan fatty acid esters, glyceryl monooleate, glyceryl monolinoleate, medium-chain triglycerides (MCT), polyglyceryl oleate, lauroyl polyoxylglyceride, stearoyl polyoxylglycerides, propylene glycol dicaprylocaprate, propylene glycol laurate, propylene glycol monolaurate, propylene glycol caprylate and propylene glycol monocaprylate, and combinations thereof, and
    the hydrophilic carrier is selected from the group consisting of polysorbate, ethanol, polyethylene glycol (PEG), glycerol, 1,2-propanediol (propylene glycol), propylene carbonate (PC), diethylene glycol monoethyl ether, and combinations thereof, and
    wherein the GEM or its pharmaceutically acceptable salt is present in an amount of 0.20% to 15% (w/w), the solvent is present in an amount of 2.5% to 60% (w/w), the surfactant system is present in an amount of 20% to 75% (w/w), and the hydrophilic carrier is present in an amount of 2.0% to 60% (w/w), based on the total weight of the formulation.

5. The method of claim 1, wherein the dosage form is administered to the subject for weeks, months or years.

6. The method of claim 5, wherein the interval between successive administrations of the dosage form is not more than three days.

7. The method of claim 5, wherein the interval between successive administrations of the dosage form is not more than two days.

8. The method of claim 5, wherein the interval between successive administrations of the dosage form is less than the normal interval at which the MTD of GEM would be administered to the subject.

9. The method of claim 1, wherein the formulation releases a fraction of the MTD for the species not greater than a fraction selected from the group consisting of ⅓, ¼, ⅕, ⅙, 1/7, 1/10, 1/12, 1/15, 1/20, and 1/40.

10. The method of claim 1, wherein the dosage form is a capsule.

11. The method of claim 10, wherein the dosage form is a soft capsule.

12. The method of claim 1, wherein the formulation comprises GEM or its pharmaceutically acceptable salt, water, glycerol, PEG, polysorbate, and oleoyl polyoxylglycerides.

13. The method of claim 1, wherein the subject is a human.

14. The method of claim 13, wherein the tumor is selected from the group consisting of breast, bladder, pancreatic, bile duct, and non-small cell lung tumors.

15. The method of claim 1, wherein the amount of GEM or its pharmaceutically acceptable salt is selected from the group consisting of not more than 2.00, not more than 1.67, and not more than 1.33 mg/kg body weight of the subject.

16. The method of claim 1, wherein in the formulation, the ratio of the solvent: the hydrophilic carrier: the surfactant system is 2:3:4.5 by weight.

17. The method of claim 1, wherein the formulation comprises GEM or its pharmaceutically acceptable salt, water, propylene glycol, PEG, polysorbate, and oleoyl polyoxylglycerides.

18. The method of claim 1, wherein the formulation is selected from the group consisting of
(i) a formulation comprising GEM or its pharmaceutically acceptable salt in an amount of about 2.00% (w/w); water in an amount of about 20.00% (w/w); glycerol and PEG together in an amount of about 32.30% (w/w); and polysorbate and oleoyl polyoxylglycerides together in an amount of about 45.70% (w/w), wherein the % (w/w) values are based on the total weight of the formulation;
(ii) a formulation comprising GEM or its pharmaceutically acceptable salt in an amount of about 2.00% (w/w); water in an amount of about 20.00% (w/w); propylene glycol and PEG in an amount of about 32.30% (w/w); and polysorbate and oleoyl polyoxylglycerides in an amount of about 45.70% (w/w), wherein the % (w/w) values are based on the total weight of the formulation; and
(iii) a formulation comprising GEM or its pharmaceutically acceptable salt in an amount of about 1.98% (w/w); water in an amount of about 19.8% (w/w); glycerol and PEG together in an amount of about 31.98% (w/w); polysorbate and oleoyl polyoxylglycerides together in an amount of about 45.25% (w/w); and TPGS in an amount of about 0.99% (w/w), wherein the % (w/w) values are based on the total weight of the formulation.

19. The method of claim 1, wherein the method is effective in inducing regression of the GEM-sensitive tumor.

20. The method of claim 1, wherein the method is effective in inhibiting growth of the GEM-sensitive tumor.

21. The method of claim 1, wherein the subject is treated with injected GEM before the oral administration of the self-emulsifying formulation of GEM.

22. The method of claim 21, wherein the injected GEM is administered at a dose at or near the MTD.

23. The method of claim 21, wherein the formulation is orally administered at a dose substantially lower than the MTD.

24. The method of claim 1, wherein the subject is treated with a different anti-tumor agent.

25. The method of claim 24, wherein the subject is not responsive to the treatment with said different anti-tumor agent.

* * * * *